United States Patent
Nathwani et al.

(10) Patent No.: US 11,077,208 B2
(45) Date of Patent: Aug. 3, 2021

(54) WILSON'S DISEASE GENE THERAPY

(71) Applicant: UCL Business Ltd, London (GB)

(72) Inventors: Amit Nathwani, London (GB); Deepak Raj, London (GB)

(73) Assignee: UCL Business Ltd, London (GB)

(*) Notice: Subject to any disclaimer, the term of this patent is extended or adjusted under 35 U.S.C. 154(b) by 342 days.

(21) Appl. No.: 16/063,451

(22) PCT Filed: Dec. 19, 2016

(86) PCT No.: PCT/GB2016/053989
§ 371 (c)(1),
(2) Date: Jun. 18, 2018

(87) PCT Pub. No.: WO2017/103624
PCT Pub. Date: Jun. 22, 2017

(65) Prior Publication Data
US 2020/0268904 A1    Aug. 27, 2020

(30) Foreign Application Priority Data
Dec. 18, 2015  (GB) .................................. 1522416

(51) Int. Cl.
| | | |
|---|---|---|
| *A61K 48/00* | (2006.01) | |
| *C12N 15/86* | (2006.01) | |
| *A01K 67/027* | (2006.01) | |
| *C12N 15/85* | (2006.01) | |

(52) U.S. Cl.
CPC ...... *A61K 48/0058* (2013.01); *A01K 67/0275* (2013.01); *C12N 15/8509* (2013.01); *C12N 15/86* (2013.01); *A01K 2217/052* (2013.01); *C12N 2750/14143* (2013.01); *C12N 2800/22* (2013.01); *C12N 2830/008* (2013.01)

(58) Field of Classification Search
CPC .......... C12Y 306/03004; C12Y 306/03; C12N 2830/85; C12N 2830/008; C12N 2800/22; C12N 2750/14143; C12N 9/14; C12N 2750/14171; C12N 15/86; C12N 15/8509; A61K 48/005; A61K 48/0058; A61K 48/0066; A61K 38/46; A01K 67/0275; A01K 2217/052
See application file for complete search history.

(56) References Cited

FOREIGN PATENT DOCUMENTS

| | | |
|---|---|---|
| CN | 103224556 A | 7/2013 |
| DE | 10156121 A1 | 5/2003 |
| KR | 2013-0098749 A | 9/2013 |
| WO | 95/08641 A1 | 3/1995 |
| WO | 2011/005968 A1 | 1/2011 |
| WO | 2012/121324 A1 | 9/2012 |
| WO | 2016/097218 A1 | 6/2016 |
| WO | 2016/097219 A1 | 6/2016 |
| WO | WO-2016097218 A1 * | 6/2016 .............. A61P 25/18 |
| WO | WO-2016097219 A1 * | 6/2016 ................ A61P 3/00 |

OTHER PUBLICATIONS

Sequence alignment SAUCA SEQ ID No. 2 and U.S. Appl. No. 16/063,451 SEQ ID No. 1 (2020). (Year: 2020).*
Murillo et al., "Long-term metabolic correction of Wilson's disease in a murine model by gene therapy," Journal of Hepatology, 64: 419-426 (2015).
Roy-Chowdhury et al., "Gene therapy of Wilson disease: A "golden" opportunity using rAAV on the 50th anniversary of the discovery of the virus," Journal of Hepatology, 64: 265-267 (2016).
McIntosh et al., "Therapeutic levels of FVIII following a single peripheral vein administration of rAAV vector encoding a novel human factor VIII variant," Blood, 121: 3335-3344 (2013).
International Search Report issued in corresponding International Patent Application No. PCT/GB2016/053989 dated Mar. 3, 2017.
Written Opinion issued in corresponding International Patent Application No. PCT/GB2016/053989 dated Mar. 3, 2017.
Search Report issued in corresponding Great Britain Patent Application No. 1522416.5 dated Sep. 28, 2016.

* cited by examiner

*Primary Examiner* — Scott Long
*Assistant Examiner* — Anjeanette Roberts
(74) *Attorney, Agent, or Firm* — Morgan, Lewis & Bockius LLP

(57) ABSTRACT

There is described a new gene therapy approach for treating Wilson's disease in which a nucleic acid molecule is used which comprises a nucleotide sequence encoding for a functional ATP7B protein wherein the nucleotide sequence has at least 85% identity to the sequence of SEQ ID NO: 1. Also described are vectors comprising the nucleotide sequence and methods and uses thereof.

10 Claims, 5 Drawing Sheets
Specification includes a Sequence Listing.

SEQUENCE LISTING

<160> NUMBER OF SEQ ID NOS: 5

<210> SEQ ID NO 1
<211> LENGTH: 4398
<212> TYPE: DNA
<213> ORGANISM: Artificial sequence
<220> FEATURE:
<223> OTHER INFORMATION: Codon optimised ATP7B nucleotide sequence

<400> SEQUENCE: 1

| | | | | | |
|---|---|---|---|---|---|
| atgcccgaac | aggagcgcca | gattactgcc | agagagggag | catccagaaa | aatcctgagc | 60 |
| aaactgtcac | tgcccacacg | agcttgggaa | cccgcaatga | agaaaagctt | cgcctttgac | 120 |
| aacgtgggat | acgagggagg | actggatgga | ctgggaccta | gctcccaggt | ggccacctct | 180 |
| acagtccgaa | tcctgggcat | gacttgccag | agttgcgtga | atcaattga | agaccggatc | 240 |
| agtaatctga | agggaatcat | tagcatgaaa | gtgtccctgg | agcagggctc | agccaccgtg | 300 |
| aagtatgtcc | ctagcgtggt | ctgcctgcag | caggtgtgcc | accagatcgg | cgatatgggg | 360 |
| ttcgaggcct | ccattgctga | agggaaagcc | gcttcttggc | ctagccggtc | cctgccagca | 420 |
| caggaagcag | tggtcaagct | gagagtggag | ggaatgacat | gccagagctg | cgtgagcagt | 480 |
| atcgaaggaa | aggtccgaaa | actgcagggc | gtggtccggg | tgaaggtctc | tctgagtaac | 540 |
| caggaggccg | tgattaccta | ccagcccatt | ctgatccagc | tgaagacct | gagggatcac | 600 |
| gtgaatgaca | tgggcttcga | ggcagccatc | aagtccaaag | tggccccact | gtctctgggg | 660 |
| cccattgaca | tcgaaagact | gcagtccacc | aacccaaaga | ggcccctgtc | aagcgccaac | 720 |
| cagaacttca | caatagtga | accctgggga | caccagggct | cacatgtggt | cacactgcag | 780 |
| ctgaggattg | acggcatgca | ctgcaagtct | tgcgtgctga | acattgagga | aaatatcggc | 840 |
| cagctgctgg | gggtgcagtc | tatccaggtc | agtctggaga | caagactgc | tcaggtgaaa | 900 |
| tacgatcctt | catgcaccag | cccagtggca | ctgcagcgcg | ctatcgaagc | actgccccct | 960 |
| ggaaatttca | aggtgagcct | gcctgacgga | gcagagggat | ccggaaccga | tcacaggtcc | 1020 |
| tctagttcac | attccccagg | atctccacca | cgaaaccagg | tgcagggaac | atgttccacc | 1080 |
| acactgattg | caatcgccgg | catgacttgc | gcctcatgcg | tgcacagcat | tgaagggatg | 1140 |
| atctctcagc | tggagggagt | gcagcagatc | tcagtcagcc | tggccgaggg | cactgctacc | 1200 |
| gtgctgtaca | atcccagtgt | catctcacct | gaggaactgc | gggctgcaat | tgaggacatg | 1260 |
| gggttcgaag | cttccgtggt | ctccgaatct | tgcagtacca | accccctggg | gaatcattcc | 1320 |
| gccggaaact | ctatggtgca | gactaccgac | gggacaccta | cttctgtgca | ggaggtcgca | 1380 |
| ccacacacag | gacgcctgcc | agccaatcat | gctcccgaca | tcctggccaa | aagcccccag | 1440 |
| tccacccggg | ctgtggcacc | tcagaagtgt | tttctgcaga | tcaaaggcat | gacctgcgcc | 1500 |
| tcttgcgtga | gcaacattga | gcggaatctg | cagaaggaag | ctggggtgct | gagcgtgctg | 1560 |
| gtcgcactga | tggccggaaa | ggctgagatc | aagtacgacc | tgaagtgat | ccagccactg | 1620 |
| gagattgccc | agttcatcca | ggatctgggc | tttgaggccg | ctgtgatgga | agactatgct | 1680 |
| gggagcgatg | gaaacattga | actgaccatc | acaggcatga | cttgtgcctc | ttgcgtgcac | 1740 |
| aacatcgaga | gtaaactgac | tagaaccaat | gggattacct | acgccagtgt | ggccctggct | 1800 |
| acatcaaagg | ctctggtgaa | attcgacccc | gagatcattg | acctaggga | catcatcaag | 1860 |
| atcattgagg | aaatcggctt | tcacgcaagc | ctgcccagc | gcaacccaaa | tgcccaccat | 1920 |
| ctggaccata | agatggagat | caagcagtgg | aagaaaagtt | tcctgtgctc | actggtgttt | 1980 |
| ggaatccccg | tcatggccct | gatgatctac | atgctgatcc | ctagcaacga | gccacaccag | 2040 |

```
tccatggtgc tggatcataa catcattcct ggcctgtcca tcctgaatct gattttcttt   2100
atcctgtgca cattcgtgca gctgctggga ggctggtact tttatgtgca ggcatataaa   2160
tcactgcgac accggagcgc caatatggac gtgctgattg tcctggcaac ctctatcgcc   2220
tacgtgtata gtctggtcat cctggtggtc gcagtggcag agaaggcaga acggagcccc   2280
gtgactttct tgataccccc tccaatgctg ttcgtgttta tcgctctggg cagatggctg   2340
gaacatctgg caaagtcaaa aaccagcgag gctctggcaa agctgatgag cctgcaggct   2400
accgaagcaa cagtggtcac tctgggagag acaacctga tcattcgcga ggaacaggtg    2460
cctatggaac tggtccagcg aggcgacatc gtgaaggtgg tcccagggg aaaattcccc    2520 gtggacggca aggtcctgga ggggaatact atggccgatg aatccctgat caccggcgag   2580
gctatgcctg tgacaaagaa accaggatca actgtcattg ctggcagcat caacgcacac   2640
gggtccgtgc tgatcaaggc cacacatgtc gggaatgaca caactctggc tcagattgtg   2700
aaactggtcg aggaagccca gatgtccaag gctcctatcc agcagctggc cgatcggttc   2760
tccggctact tcgtgccctt catcattatc atgtctacac tgactctggt ggtctggatt   2820
gtgatcggat tcattgactt tggcgtggtc cagagatatt ttcccaaccc taataagcac   2880
atcagccaga ccgaagtgat catcaggttc gcatttcaga ccagtattac agtgctgtgc   2940
atcgcctgcc catgttcact ggggctggct accccacag cagtgatggt cggaacaggg    3000
gtggcagcac agaacggcat cctgatcaag gcgggaaac ccctggagat ggcccacaag    3060
atcaaaactg tgatgtttga caaaactggg accattacac atggagtgcc acgcgtcatg   3120
cgagtgctgc tgctgggcga tgtggcaacc ctgcctctga aaaggtcct ggcagtggtc    3180 ggaacagcag aggctagctc cgaacaccca ctggggtgg ccgtcacaaa gtactgcaaa    3240
gaggaactgg gcactgagac cctggggtat tgtactgact ccaggcagt gccaggatgc    3300 ggaatcggat gtaaagtctc taacgtgaa gggattctgg ctcacagtga gcggccctg    3360 agcgcacctg catcccatct gaatgaagca ggaagcctgc cagcagagaa ggacgctgtg   3420
cctcagacct tttccgtcct gatcggcaac agagaatggc tgcggagaaa tgggctgaca   3480
atttctagtg acgtgtccga tgccatgaca gatcacgaga tgaaaggcca gactgcaatt   3540
ctggtggcca tcgacggagt cctgtgcggc atgattgcta tcgcagatgc cgtgaagcag   3600
gaggctgcac tggccgtcca taccctgcag tctatgggcg tggacgtggt cctgatcacc   3660
ggggataacc ggaaaacagc tagagcaatt gccactcaag tgggcatcaa taaggtgttc   3720
gctgaagtcc tgcctagcca caaggtcgca aaagtgcagg agctgcagaa caagggcaag   3780
aaagtcgcca tggtgggaga cggcgtgaat gatagcccag ctctggcaca ggcagacatg   3840
ggagtcgcta ttgggacagg aactgacgtg gcaatcgagg ccgctgatgt ggtcctgatt   3900
aggaatgacc tgctggatgt ggtcgcttct attcatctga gtaagaggac agtgaggcgc   3960
attcgcatca acctggtgct ggccctgatc tacaatctgg tgggcatccc catcgcagca   4020 ggcgtgtttta tgccaattgg gatcgtcctg cagccctgga tgggctcagc tgcaatggcc   4080
gcttcaagcg tgagcgtggt cctgtcctct ctgcagctga aatgctacaa gaaaccagat   4140
ctggagcggt acgaagctca ggcacacgga catatgaagc cctgaccgc ttcccaggtg    4200 tctgtccaca tcggcatgga cgatagatgg agggacagcc caagggcaac tccatgggat   4260
caggtcagtt acgtgagcca ggtcagcctg agttcactga ccagcgacaa gccctcccgc   4320
cattctgcag ccgctgatga cgacggggac aagtggagcc tgctgctgaa cgggagggac   4380
```

```
gaagaacagt acatttga                                                    4398

<210> SEQ ID NO 2
<211> LENGTH: 20
<212> TYPE: DNA
<213> ORGANISM: Artificial sequence
<220> FEATURE:
<223> OTHER INFORMATION: Primer for endogenous ATP7B

<400> SEQUENCE: 2
cacatggctc tgtgctcatt                                                    20

<210> SEQ ID NO 3
<211> LENGTH: 20
<212> TYPE: DNA
<213> ORGANISM: Artificial sequence
<220> FEATURE:
<223> OTHER INFORMATION: Primer for endogenous ATP7B

<400> SEQUENCE: 3
tctgagcctc ttccaccagt                                                    20

<210> SEQ ID NO 4
<211> LENGTH: 20
<212> TYPE: DNA
<213> ORGANISM: Artificial sequence
<220> FEATURE:
<223> OTHER INFORMATION: Primer for codon optimised ATP7B

<400> SEQUENCE: 4
accggaaaac agctagagca                                                    20

<210> SEQ ID NO 5
<211> LENGTH: 20
<212> TYPE: DNA
<213> ORGANISM: Artificial sequence
<220> FEATURE:
<223> OTHER INFORMATION: Primer for codon optimised ATP7B

<400> SEQUENCE: 5
gtggctaggc aggacttcag                                                    20
```

WILSON'S DISEASE GENE THERAPY

The present application is a national stage application of PCT/GB2016/053989 filed Dec. 19, 2016, claiming priority to UK 1522416.5 filed Dec. 18, 2015.

A computer readable text file, entitled "SequenceListing.txt," created on or about Jun. 18, 2018 with a file size of about 7 kb contains the sequence listing for this application and is hereby incorporated by reference in its entirety.

FIELD OF THE INVENTION

The invention relates to a new gene therapy approach for treating Wilson's disease.

BACKGROUND TO THE INVENTION

Wilson's disease is a rare autosomal recessive disorder with a global incidence considered to be 1 in 30,000. It leads to accumulation of copper in various organs such as the liver, basal ganglia, and cornea. Normally, dietary copper that enters hepatocytes is released into the bile by the ATP7B protein. However, in Wilson's disease, a homozygous mutation in the ATP7B gene leads to loss of biliary secretion of copper and accumulation of this metal in the liver and cornea, and to a lesser extent the brain, leading to cell injury and apoptosis. Patients with Wilson's disease usually present between the age of 6 and 20 years but as with other liver diseases, chronic hepatic injury does not cause many symptoms, and the only abnormality usually seen is an elevated level of aminotransferases or hepatomegaly. Long-term chelation with penicillamine is the initial treatment of choice but a substantial number of patients experience side-effects or complications, such as drug-induced lupus or myasthenia. Compliance with the drug is therefore poor. Alternatives to penicillamine include trientine hydrochloride, and to a lesser extent tetrathiomolybdate. Patients who respond to chelation therapy may be treated with zinc to maintain stable copper levels in the body. Zinc stimulates metallothionein, a protein in gut cells that binds copper and prevents its absorption and transport to the liver. These treatments are regarded as non-curative as the metabolic defects in Wilson's disease is not corrected by chelation therapy or treatment with zinc. Liver transplantation offers the possibility of cure, but is associated with a significant morbidity and mortality.

There is therefore a need for therapeutic strategies that can reverse the underlying metabolic defect. Transplantation of normal hepatocytes in animal models of Wilson's disease has been shown to be efficacious but only transiently and is associated with: (a) problems of engraftment and proliferation of donor cells necessitating pre-conditioning with radiation, portal vein embolization or partial resection of liver; (b) the need for modulation of immune reaction and vascular changes; and (c) the lack of steady supply of healthy unused donor livers to isolate hepatocytes (Irani A N et al, Mol Ther 3:302-309; Park S M et al, Cell Transplant 15:13-22; Hughes R D et al; Transplantation 93:342-347).

In contrast, gene therapy for Wilson's disease offers the potential for a cure through persistent, endogenous production of ATP7B following the transfer of a normal copy of the ATP7B gene to an affected patient.

Previously, lentiviral transfer of ATP7B was attempted in a rat model (Merle U et al, Scand J Gastroenterol 41:974-982) as well as in prenatal animals in a mouse model of the disease (Roybal J L et al, Gene Ther 19:1085-1094), but poor transduction of affected tissue and limited phenotypic correction was observed.

The inventors have developed a gene therapy approach using adeno-associated viral vectors (AAV) to mediate transfer and expression of the ATP7B gene. As Wilson's disease arises from a defect in a single gene, relatively low levels of enzyme correction will offer reduced storage of copper. The inventor's approach entails liver mediated expression of ATP7B following in-vivo, AAV mediated gene transfer of hepatocytes, which results in tolerance to the transgenic protein, thereby reducing the risk of developing neutralising antibodies to ATP7B.

SUMMARY OF THE INVENTION

In a first aspect of the invention, there is provided a nucleic acid molecule comprising a nucleotide sequence encoding for a functional ATP7B protein wherein the nucleotide sequence has at least 85% identity to the sequence of SEQ ID NO: 1.

SEQ ID NO: 1 is a codon optimised nucleotide sequence encoding for an ATP7B protein. The inventors have surprisingly found that the novel codon optimised sequence of SEQ ID NO: 1 results in higher levels of expression of the ATP7B transcript in hepatocytes transduced with an AAV vector under the control of a liver specific promoter, than levels of the wild-type transcript.

The nucleotide sequence has at least 85% identity to the sequence of SEQ ID NO: 1. In some embodiments, the nucleotide sequence has at least 86% identity to the sequence of SEQ ID NO: 1. In other embodiments, the nucleotide sequence has at least 87% identity to the sequence of SEQ ID NO: 1. In particular embodiments, the nucleotide sequence has at least 88% identity to the sequence of SEQ ID NO: 1. In further embodiments, the nucleotide sequence has at least 89% identity to the sequence of SEQ ID NO: 1. In some embodiments, the nucleotide sequence has at least 90% identity to the sequence of SEQ ID NO: 1. In other embodiments, the nucleotide sequence has at least 91% identity to the sequence of SEQ ID NO: 1. In particular embodiments, the nucleotide sequence has at least 92% identity to the sequence of SEQ ID NO: 1. In further embodiments, the nucleotide sequence has at least 93% identity to the sequence of SEQ ID NO: 1. In some embodiments, the nucleotide sequence has at least 94% identity to the sequence of SEQ ID NO: 1. In other embodiments, the nucleotide sequence has at least 95% identity to the sequence of SEQ ID NO: 1. In particular embodiments, the nucleotide sequence has at least 96% identity to the sequence of SEQ ID NO: 1. In further embodiments, the nucleotide sequence has at least 97% identity to the sequence of SEQ ID NO: 1. In some embodiments, the nucleotide sequence has at least 98% identity to the sequence of SEQ ID NO: 1. In other embodiments, the nucleotide sequence has at least 99% identity to the sequence of SEQ ID NO: 1. In particular embodiment, the nucleotide sequence has the sequence of SEQ ID NO: 1.

A functional ATP7B protein is an ATPase which transports copper into, and out of cells. Suitable methods for assaying for ATP7B activity are well known to those skilled in the art.

In a second aspect of the invention there is provided a vector for expressing ATP7B protein.

The vector comprises the nucleic acid molecule described above. This means that the vector contains a nucleotide sequence encoding for a functional ATP7B protein so that when this sequence is expressed, a functional ATP7B protein is produced by the cell in which the vector is contained.

The sequence of SEQ ID NO: 1 is a codon optimised ATP7B nucleotide sequence. This sequence has not been codon optimised in a normal way. Instead, the codons have been selected based on the codons used for proteins which are expressed at a high level in the liver. The reason for this is that the vector is normally expressed in the liver. This special codon optimisation process has been found to produce a nucleotide sequence which gives surprisingly high expression.

The nucleotide sequence encoding for a ATP7B protein is preferably between 4373 and 4423 nucleotides in length. In some embodiments, the nucleotide sequence encoding for a functional ATP7B protein is between 4378 and 4418 nucleotides in length. In other embodiments, the nucleotide sequence encoding for a functional ATP7B protein is between 4383 and 4413 nucleotides in length. In particular embodiments, the nucleotide sequence encoding for a functional ATP7B protein is between 4388 and 4408 nucleotides in length.

Preferably the vector further comprises a promoter. The promoter causes expression of the nucleotide sequence encoding for a functional ATP7B protein. Any appropriate promoter may be used, such as HLP, LP1, HCR-hAAT, ApoE-hAAT, and LSP. These promoters are described in more detail in the following references: HLP: McIntosh J. et al., Blood 2013 Apr. 25, 121(17):3335-44; LP1: Nathwani et al., Blood. 2006 Apr. 1, 107(7): 2653-2661; HCR-hAAT: Miao et al., Mol Ther. 2000; 1: 522-532; ApoE-hAAT: Okuyama et al., Human Gene Therapy, 7, 637-645 (1996); and LSP: Wang et al., Proc Natl Acad Sci USA. 1999 Mar. 30, 96(7): 3906-3910. A preferred promoter is also described in WO 2011/005968. Preferably, the promoter is a liver specific promoter. In particular embodiments, the promoter is an HLP promoter.

The vector may be any appropriate vector for expressing the ATP7B protein, including viral and non-viral vectors. Viral vectors include a parvovirus, an adenovirus, a retrovirus, a lentivirus or a herpes simplex virus. The parvovirus may be an adenovirus-associated virus (AAV). The vector is preferably a recombinant adeno-associated viral (rAAV) vector or a lentiviral vector. More preferably, the vector is a rAAV vector.

A vector according to the invention may be a gene delivery vector. Such a gene delivery vector may be a viral gene delivery vector or a non-viral gene delivery vector.

Accordingly, the present invention provides gene delivery vectors based on animal parvoviruses, in particular dependoviruses such as infectious human or simian AAV, and the components thereof (e.g., an animal parvovirus genome) for use as vectors for introduction and/or expression of an ATP7B protein in a mammalian cell. The term "parvoviral" as used herein thus encompasses dependoviruses such as any type of AAV.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience, the present invention is further exemplified and described herein by reference to AAV. It is, however, understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild type (wt) AAV infection in mammalian cells the Rep genes (i.e. encoding Rep78 and Rep52 proteins) are expressed from the P5 promoter and the P19 promoter, respectively, and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

In an AAV suitable for use as a gene therapy vector, the vector genome typically comprises a nucleic acid to be packaged for delivery to a target cell. According to this particular embodiment, the heterologous nucleotide sequence is located between the viral ITRs at either end of the vector genome. In further preferred embodiments, the parvovirus (e.g. AAV) cap genes and parvovirus (e.g. AAV) rep genes are deleted from the template genome (and thus from the virion DNA produced therefrom). This configuration maximizes the size of the nucleic acid sequence(s) that can be carried by the parvovirus capsid.

According to this particular embodiment, the nucleic acid is located between the viral ITRs at either end of the substrate. It is possible for a parvoviral genome to function with only one ITR. Thus, in a gene therapy vector of the invention based on a parvovirus, the vector genome is flanked by at least one ITR, but, more typically, by two AAV ITRs (generally with one either side of the vector genome, i.e. one at the 5' end and one at the 3' end). There may be intervening sequences between the nucleic acid in the vector genome and one or more of the ITRs.

Preferably, the nucleotide sequence encoding a functional ATP7B protein (for expression in the mammalian cell) will be incorporated into a parvoviral genome located between two regular ITRs or located on either side of an ITR engineered with two D regions.

AAV sequences that may be used in the present invention for the production of AAV gene therapy vectors can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chiorini el al, 1997; Srivastava et al, 1983; Chiorini et al, 1999; Rutledge et al, 1998; and Wu et al, 2000. AAV serotype 1, 2, 3, 4, 5, 6, 7, 8 or 9 may be used in the present invention. However, AAV serotypes 1, 5 or 8 are preferred sources of AAV sequences for use in the context of the present invention. The sequences from the AAV serotypes may be mutated or engineered when being used in the production of gene therapy vectors.

Preferably, the AAV ITR sequences for use in the context of the present invention are derived from AAV1, AAV2, AAV4 and/or AAV6. Likewise, the Rep (Rep78 and Rep52) coding sequences are preferably derived from AAV1, AAV2, AAV4 and/or AAV6. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al, 1999). Moreover, the Rep sequences and ITRs of many AAV serotypes are known to efficiently cross-complement (i.e., functionally substitute) corresponding sequences from other serotypes in production of AAV particles in mammalian cells. US 2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped AAV particles comprising the capsid proteins of a serotype (e.g., AAV1, 5 or 8) and the Rep and/or ITR sequences of another AAV serotype (e.g., AAV2). Such pseudotyped rAAV particles are a part of the present invention.

Modified "AAV" sequences also can be used in the context of the present invention, e.g. for the production of AAV gene therapy vectors. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of AAV5 or pseudotyped AAV5 vectors. For example, the start codon of the Rep sequences can be modified, VP splice sites can be modified or eliminated, and/or the VP1 start codon and nearby nucleotides can be modified to improve the production of AAV5 vectors.

Thus, the viral capsid used in the invention may be from any parvovirus, either an autonomous parvovirus or dependovirus, as described above. Preferably, the viral capsid is an AAV capsid (e.g., AAV1, AAV2, AAV3, AAV4, AAV5 or AAV6 capsid). In general, the AAV1 capsid or AAV6 capsid are preferred. The choice of parvovirus capsid may be based on a number of considerations as known in the art, e.g., the target cell type, the desired level of expression, the nature of the heterologous nucleotide sequence to be expressed, issues related to viral production, and the like. For example, the AAV1 and AAV6 capsid may be advantageously employed for skeletal muscle; AAV1, AAV5 and AAV8 for the liver and cells of the central nervous system (e.g., brain); AAV5 for cells in the airway and lung or brain; AAV3 for bone marrow cells; and AAV4 for particular cells in the brain (e.g., appendable cells).

It is within the technical skills of the skilled person to select the most appropriate virus, virus subtype or virus serotype. Some subtypes or serotypes may be more appropriate than others for a certain type of tissue.

For example, liver-specific expression of a nucleic acid of the invention may advantageously be induced by AAV-mediated transduction of liver cells. Liver is amenable to AAV-mediated transduction, and different serotypes may be used (for example, AAV1, AAV5 or AAV8). Transduction of muscle may be accomplished by administration of an AAV encoding a nucleic acid via the blood stream. Thus, intravenous or intra-arterial administration is applicable.

A parvovirus gene therapy vector prepared according to the invention may be a "hybrid" particle in which the viral TRs and viral capsid are from different parvoviruses. Preferably, the viral TRs and capsid are from different serotypes of AAV. Likewise, the parvovirus may have a "chimeric" capsid (e.g., containing sequences from different parvoviruses, preferably different AAV serotypes) or a "targeted" capsid (e.g., a directed tropism).

In the context of the invention "at least one parvoviral ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans-acting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. A parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Preferably, however, two or another even number of regular ITRs are used. Most preferably, two ITR sequences are used. A preferred parvoviral ITR is an AAV ITR. For safety reasons it may be desirable to construct a parvoviral (AAV) vector that is unable to further propagate after initial introduction into a cell. Such a safety mechanism for limiting undesirable vector propagation in a recipient may be provided by using AAV with a chimeric ITR as described in US 2003148506.

Those skilled in the art will appreciate that the viral Rep protein(s) used for producing an AAV vector of the invention may be selected with consideration for the source of the viral ITRs. For example, the AAV5 ITR typically interacts more efficiently with the AAV5 Rep protein, although it is not necessary that the serotype of ITR and Rep protein(s) are matched.

The ITR(s) used in the invention are typically functional, i.e. they may be fully resolvable and are preferably AAV sequences, with serotypes 1, 2, 3, 4, 5 or 6 being preferred. Resolvable AAV ITRs according to the present invention need not have a wild-type ITR sequence (e.g., a wild-type sequence may be altered by insertion, deletion, truncation or missense mutations), as long as the ITR mediates the desired functions, e.g., virus packaging, integration, and/or provirus rescue, and the like.

Advantageously, by using a gene therapy vector as compared with previous approaches, the restoration of protein synthesis, i.e. ATP7B synthesis, is a characteristic that the transduced cells acquire permanently or for a sustained period of time, thus avoiding the need for continuous administration to achieve a therapeutic effect.

Accordingly, the vectors of the invention therefore represent a tool for the development of strategies for the in vivo delivery of an ATP7B nucleotide sequence, by engineering the nucleic acid within a gene therapy vector that efficiently transduces an appropriate cell type, such as a liver cell.

Preferably, the vector is a single stranded vector rather than a self-complementary vector. Surprisingly, this has been shown to give better protein expression.

The vector may further comprise a poly A tail. Preferably, this is positioned downstream of the nucleotide sequence encoding for a functional ATP7B protein. Preferably, the poly A tail is a small synthetic Poly A, identical to the one used in McIntosh J. et al., Blood (2013): 121(17): 3335-44 in the construct expressing FVIII V3.

The vector may comprise other elements to allow the functional ATP7B protein to be expressed. Such elements are well known to a person skilled in the art.

Preferably, the nucleic acids described above are isolated.

It would be well with the capabilities of a skilled person to produce the nucleic acid molecules described above. This could be done, for example, using chemical synthesis of a given sequence.

Further, a skilled person would readily be able to determine whether a nucleic acid expresses a functional protein. Suitable methods would be apparent to those skilled in the art. For example, one suitable in vitro method involves inserting the nucleic acid into a vector, such as a lentiviral or an AAV vector, transducing host cells, such as 293T or HeLa cells, with the vector, and assaying for ATP7B activity. Alternatively, a suitable in vivo method involves transducing a vector containing the nucleic acid into an animal model for Wilson's disease and assaying for functional ATP7B in the plasma of the mice. The animal models for Wilson's disease are: 1) the Long Evans Cinnamon rat, which has a large deletion in the ATP7B gene (Terada K, Sugiyama T. Pediatr Int. 1999 August; 41(4):414-8); 2) the Jackson's toxic milk mouse, which has a point mutation in the ATP7B coding sequence (Roberts E A, Robinson B H, Yang S. Mol Genet Metab. 2008 January; 93(1):54-65); and 3) an ATP7B$^{-/-}$ mouse (Huster D, Finegold M J, Morgan C T, Burkhead J L, Nixon R, Vanderwerf S M, Gilliam C T, Lutsenko S. Am J Pathol. 2006 February; 168(2):423-34). Further, suitable methods are described in more detail below.

The nucleic acid can be any type of nucleic acid composed of nucleotides. The nucleic acid should be able to be expressed so that a protein is produced. Preferably, the nucleic acid is DNA or RNA.

The invention also provides a host cell comprising any one of the nucleic acid molecules or vectors described above. Preferably, the vector is capable of expressing the ATP7B nucleotide sequence in the host. The host may be any suitable host.

As used herein, the term "host" refers to organisms and/or cells which harbour a nucleic acid molecule or a vector of the invention, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host. A host cell may be in the form of a single cell, a population of similar or different cells, for example in the form of a culture (such as a liquid culture or a culture on a solid substrate), an organism or part thereof.

A host cell according to the invention may permit the expression of a nucleic acid molecule of the invention. Thus, the host cell may be, for example, a bacterial, a yeast, an insect or a mammalian cell.

In addition, the invention provides a transgenic animal comprising cells comprising the nucleic acid molecule encoding for a functional ATP7B protein described above or a vector described above. Preferably the animal is a non-human mammal, especially a primate. Alternatively, the animal may be a rodent, especially a mouse; or may be canine, feline, ovine or porcine.

In one aspect, the invention provides a pharmaceutical composition comprising a nucleic acid molecule or a vector of the invention and one or more pharmaceutically acceptable excipients. The one or more excipients include carriers, diluents and/or other medicinal agents, pharmaceutical agents or adjuvants, etc.

The invention also provides a method of treating Wilson's disease comprising administering a therapeutically effective amount of a vector as described above to a patient suffering from Wilson's disease. Preferably, the patient is human.

When Wilson's disease is "treated" in the above method, this means that one or more symptoms of Wilson's disease are ameliorated. It does not mean that the symptoms of Wilson's disease are completely remedied so that they are no longer present in the patient, although in some methods, this may be the case. The method of treating results in one or more of the symptoms of Wilson's disease being less severe than before treatment.

A "therapeutically effective amount" refers to an amount effective, at dosages and for periods of time necessary, to achieve the desired therapeutic result, such as raising the level of functional ATP7B in a subject (so as to lead to functional ATP7B production to a level sufficient to ameliorate the symptoms of Wilson's disease).

Delivery of a nucleic acid or vector of the invention to a host cell in vivo may result in an increase of functional ATP7B in the host, for example to a level that ameliorates one or more symptoms of Wilson's disease.

It has been found that when the method of treatment of the invention is used, it can cause an increase in the level of functional ATP7B in the subject. In some embodiments, the method of treatment of the invention causes an increase in the level of functional ATP7B to about a normal level (i.e. the level found in a normal healthy subject). In one embodiment, the method of treatment of the invention causes an increase in the level of functional factor ATP7B to, at most, normal levels.

Further, the invention provides the nucleic acid molecule encoding for a functional ATP7B protein as described above, or a vector as described above for use in therapy, for example, in the treatment of Wilson's disease.

In addition, the invention provides the use of the nucleic acid molecule encoding for a functional ATP7B protein as described above or a vector as described above in the manufacture of a medicament for treating Wilson's disease.

The invention also provides a method for delivery of a nucleotide sequence encoding a functional ATP7B protein to a subject, which method comprises administering to the said subject a nucleic acid molecule encoding a functional ATP7B protein as described above or a vector as described above.

In the description above, the term "identity" is used to refer to the similarity of two sequences. For the purpose of this invention, it is defined here that in order to determine the percent identity of two nucleotide sequences, the sequences are aligned for optimal comparison purposes (e.g., gaps can be introduced in the sequence of a first nucleic acid for optimal alignment with a second amino or nucleic acid sequence). The nucleotide residues at nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length. A sequence comparison is typically carried out over the entire length of the two sequences being compared.

The skilled person will be aware of the fact that several different computer programs are available to determine the homology or identity between two sequences. For instance, a comparison of sequences and determination of percent identity between two sequences can be accomplished using a mathematical algorithm. In a preferred embodiment, the percent identity between two nucleic acid sequences is determined using the sequence alignment software Clone Manager 9 (Sci-Ed software—scied.com) using global DNA alignment; parameters: both strands; scoring matrix: linear (mismatch 2, OpenGap 4, ExtGap 1).

Alternatively, the percent identity between two nucleic acid sequences (or two amino acid sequences) is determined using the Needleman and Wunsch (1970) algorithm which has been incorporated into the GAP program in the Accelrys GCG software package (available at accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6.

The nucleic acid sequences of the present invention can further be used as a "query sequence" to perform a search against public databases to, for example, identify other family members or related sequences. Such searches can be performed using the BLASTN programs (version 2.0) of Altschul, et al, 1990. To obtain gapped alignments for comparison purposes, Gapped BLAST can be utilized as described in Altschul et al, 1997. When utilizing BLAST and Gapped BLAST programs, the default parameters of the respective programs (e.g. BLASTN) can be used. See the homepage of the National Center for Biotechnology Information at ncbi.nlm.nih.gov/.

All patent and literature references cited in the present specification are hereby incorporated by reference in their entirety.

A skilled person will appreciate that all aspects of the invention, whether they relate to, for example, the nucleic acid, the vector, the host cell or the use, are equally applicable to all other aspects of the invention. In particular, aspects of the method of treatment, for example, the administration of the nucleic acid or vector, may have been described in greater detail than in some of the other aspects of the invention, for example, relating to the use of the nucleic acid or vector for treating Wilson's disease. However, the skilled person will appreciate where more detailed information has been given for a particular aspect of the invention, this information is generally equally applicable to other aspects of the invention. Further, the skilled person will also appreciate that the description relating to the method of treatment is equally applicable to the use of the nucleic acid or vector in treating Wilson's disease.

DETAILED DESCRIPTION OF THE INVENTION

The invention will now be described in detail by way of example only with reference to the figures in which:

FIG. 1 shows a codon optimised version of ATP7B, expressed by the HLP promoter, to be packaged into an AAV vector.

FIG. 2 shows an alkaline gel analysis of a single stranded AAV8-HLP-ATP7B vector at different titres (lanes 2-4) and illustrates that it is well packaged, with a prominent full length genome and some partial genomes. A small and well packaged FIX vector (lane 1) is used as a control and lane 5 is DNA size marker.

FIG. 3 illustrates that when Huh7 liver cells were transduced with an ssAAV8-HLP-codop-hATP7B vector, they expressed similar levels of endogenous ATP7B transcript (top left panel), but high levels of the codop-hATP7B compared to un-transduced cells (top right panel). Expression of the codop-hATP7B transcript was found to increase in a dose-dependent manner (bottom panel).

FIG. 4 shows that by western blot (top panel) as well as by immunofluorescence (bottom panel), a hATP7B transgenic protein is detected in the liver of a Wilson's rat model (LEC) following vector administration. LEA rats serve as a control. Rat ATP7B does not cross react with the anti-hATP7B.

The overriding goal of the inventors' research program is to establish a cure for Wilson's disease that is safe, effective and widely available. In pursuit of this goal, the inventors have developed a liver directed AAV gene transfer approach with a unique codon optimised ATP7B sequence.

Figure 1:
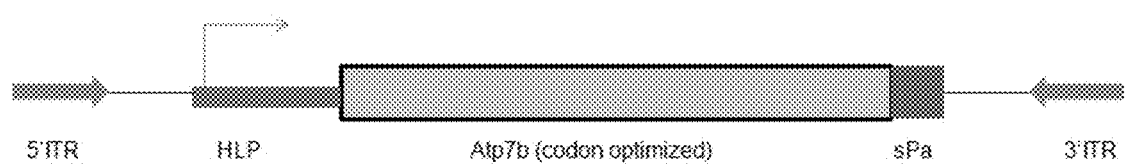
Figure 2:
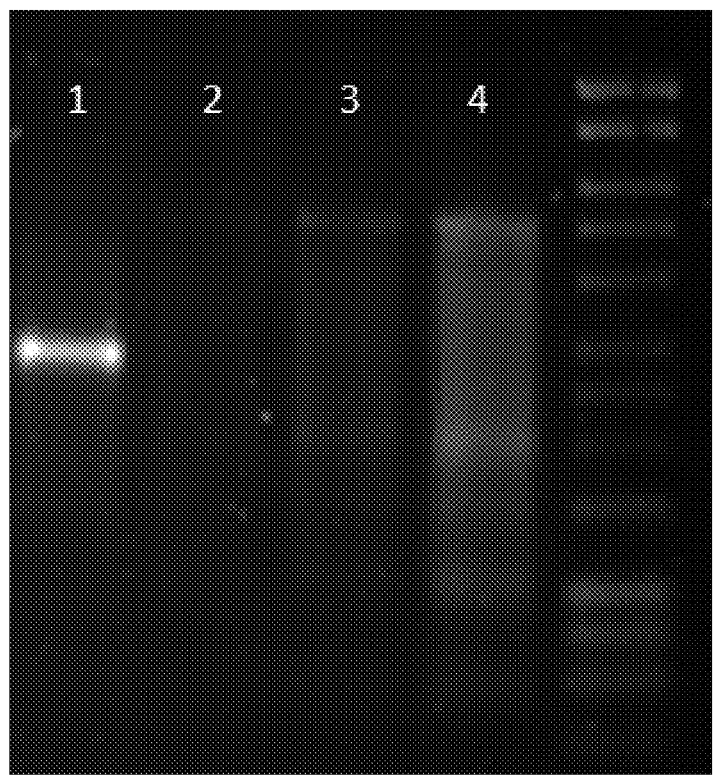

The 5.1 kb oversized rAAV-Atp7b expression cassette (schematic shown in FIG. 1) containing the codon optimised Atp7b cDNA was packaged with serotype 8 capsid using a conventional HEK293T transient transfection method, with production efficiency of ~1×10$^4$ AAV-Atp7b particles/293T. Assessment of viral DNA extracted from rAAV-Atp7b showed a single band of ~5 kb on an alkaline agarose gel, which is the expected size (FIG. 2).

Analysis of the codon optimised Atp7b transgene following transient transfection of HuH7 liver hepatoma cell lines showed (FIG. 3) significant but dose dependent increase in transgenic Atp7b transcript.

Figure 4:
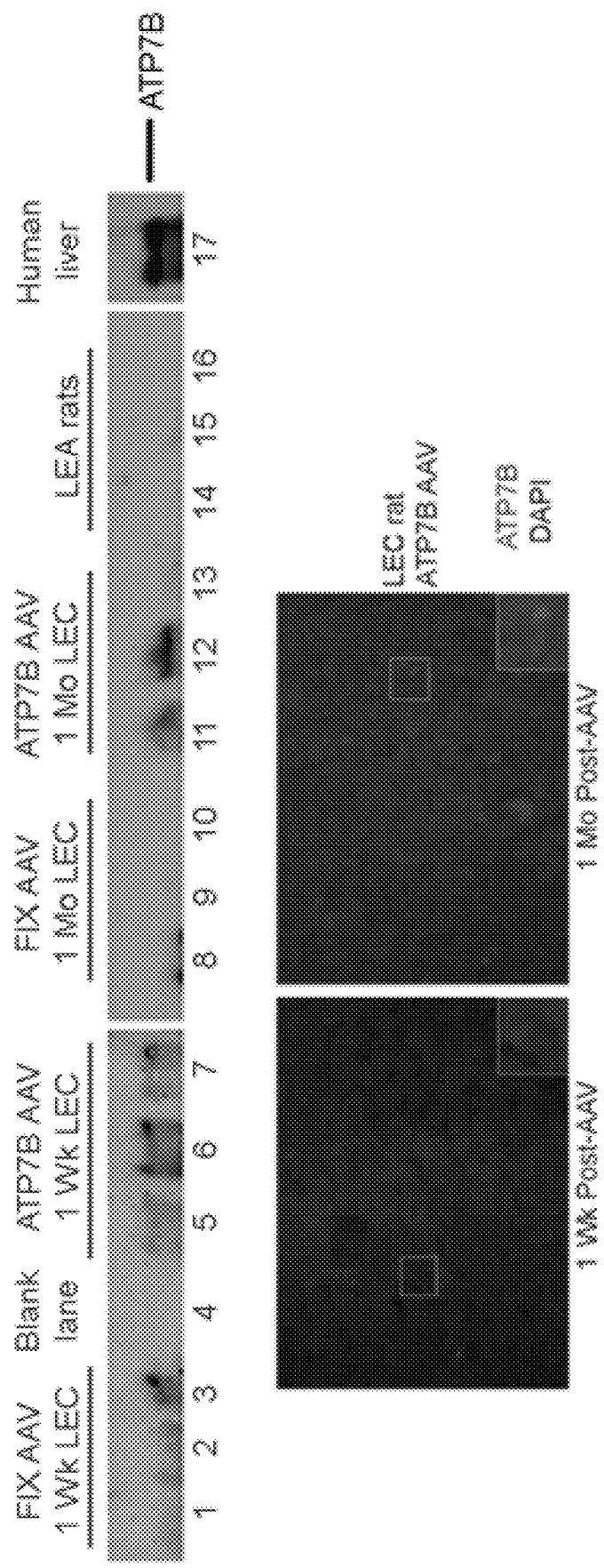
Figure 5:
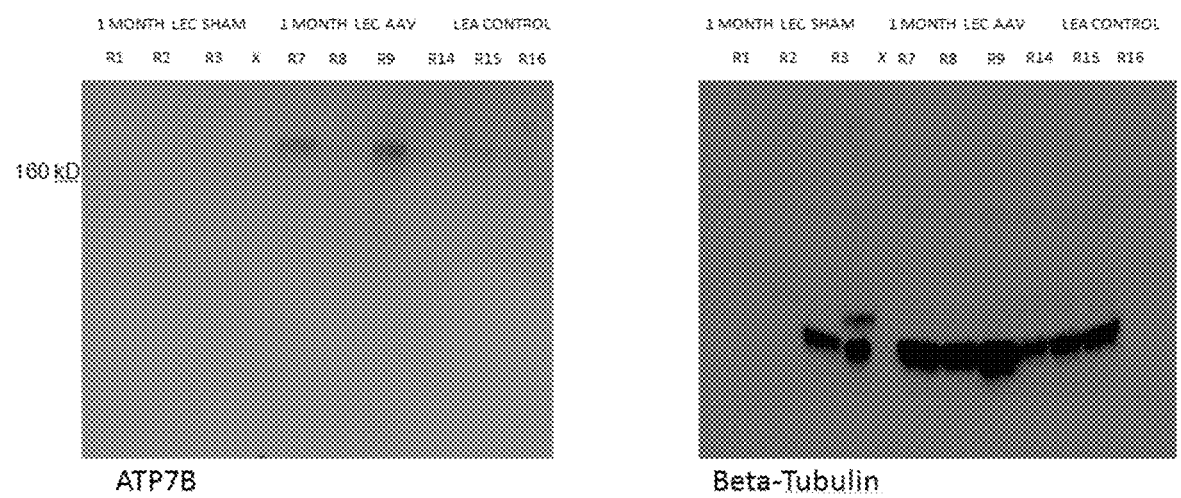
FIG. 5 shows the detailed analysis of liver tissues and illustrates that a single full-length ATP7B transgenic protein product is detected (left panel). A loading control of beta-tubulin is shown (right panel).
Figure 6:
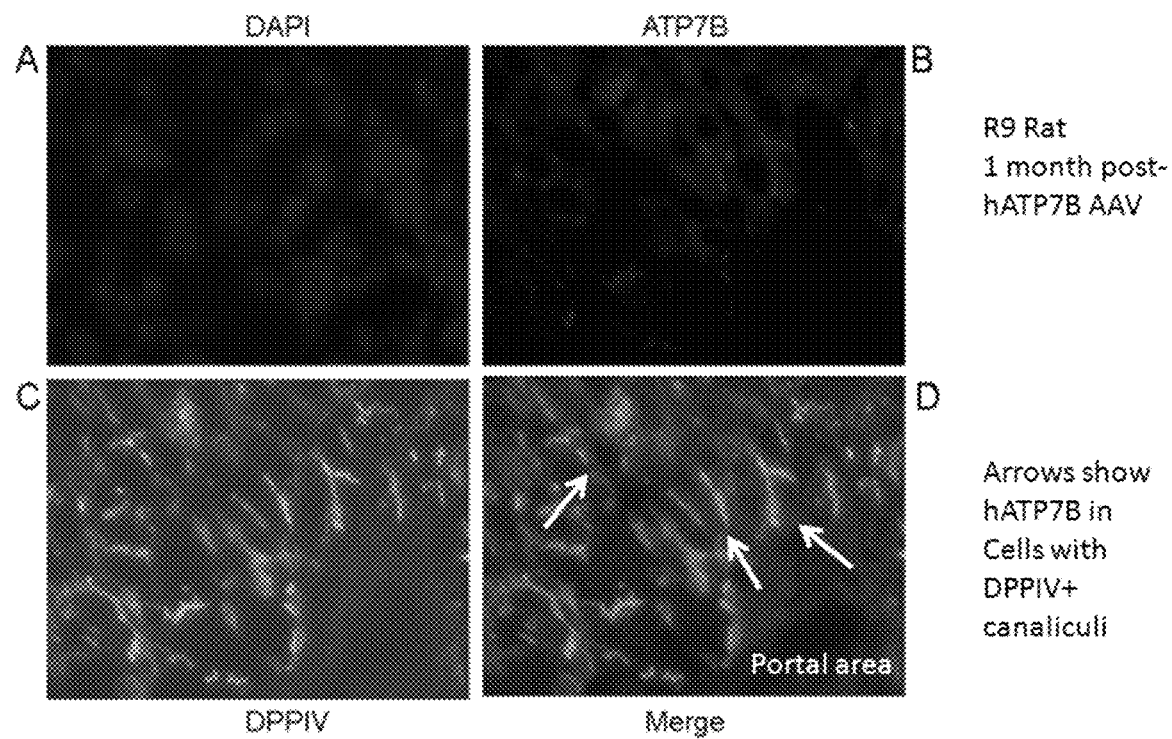
FIG. 6 illustrates that ATP7B (red) is expressed specifically in hepatocytes in rat liver following vector administration, and not in other cell types such as bile canalicular epithelium (green).
Figure 7:
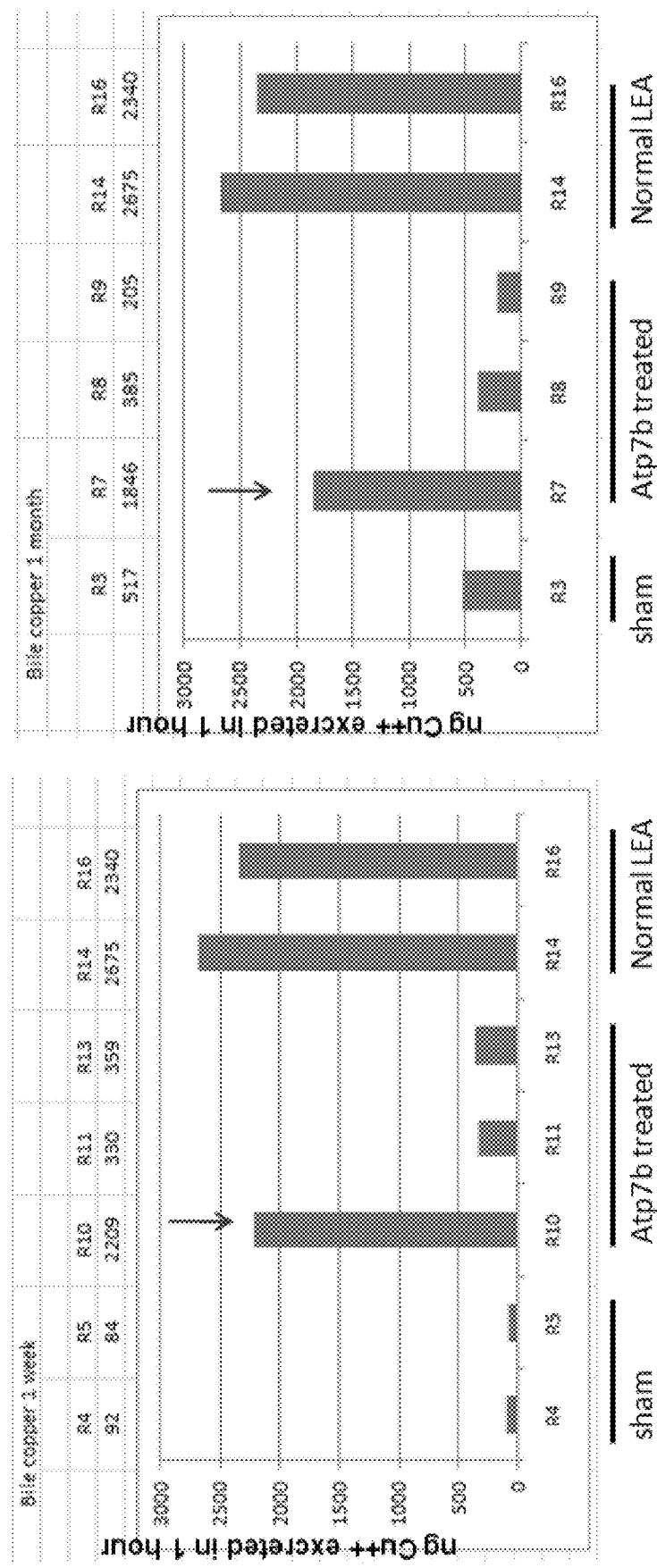
FIG. 7 shows the phenotypic correction of bile copper levels is seen in 2/6 vector-treated animals (R10 and R7). As controls, are untreated animals (sham), and normal animals (normal LEA).

Tail vein injection of ssAAV-HLP-Atp7b vector into 7-9 week old Long Evans Cinnamon rats leads to expression of Atp7b protein in the livers of these animals (FIG. 4: Top panel). Expression of Atp7b was highest 1 month post administration, and was observed in about 10% of hepatocytes (FIG. 4: Bottom panel). Western blot analysis of liver tissues of LEC rats showed specific expression of Atp7b in vector administered animals, and not in sham treated or untreated animals. The Atp7b protein is the right length, with no evidence of smaller protein products being expressed (FIG. 5, left panel). Beta tubulin blotting is used as a control (FIG. 5, right panel). Atp7b expression in liver cells of vector-administered animals was localized to hepatocytes; no expression of Atp7b is found in portal vein endothelium, or in DPPIV+ bile canalicular epithelium (FIG. 6). Importantly, bile copper expression following a single bolus of copper histidine administration was normalized in 2/6 vector administered LEC rats (FIG. 7), showing that the ssAAV-HLP-Atp7b vector can mediate phenotypic correction.

The advantages of the present invention are that:
1. A single peripheral vein infusion of AAV encoding Atp7b can result in long-term expression of Atp7b in patients with Wilson's disease. Stable long-term expression of Atp7b following AAV mediated gene transfer, will exert a more pronounced clinic benefit than possible with current therapy thereby improving the prospects of preventing organ transplantation and improvement in life expectancy of patients with Wilson's disease;
2. More potent expression from the codon optimised expression cassette resulting in a therapeutic benefit from using lower doses of AAV vector; and
3. Expression of Atp7b from the liver will reduce the risk of developing neutralising antibodies to this protein.

An initial evaluation has shown that transduction of hepatocytes with an AAV vector containing codon optimised Atp7b under the control of a liver specific promoter resulted in expression of transgenic Atp7b in homozygous Atp7b –/– rats at a level that was 5% higher than that observed in LEA control rats, which was unexpected based on the prior art.

Materials and Methods:

Production of ssAAV-HLP-Atp7b vector stock: ssAAV vector particles were produced by transfecting HEK293T cells (~8×10$^8$ in a 10-stack cell factory) with the plasmids pssAAV-HLP-Atp7b, HGTI and pCR21+LTAAVhelp2-8 (both prepared to large scale by Aldevron, Fargo, ND). The first plasmid contains the entire ssAAV vector genome, the second contains the necessary adenovirus helper sequences, and the third plasmid contains AAV serotype 2 rep and serotype 8 cap genes. Twenty four hours later, the medium was aspirated and replaced with DMEM with no additives. Seventy two hours after transfection, cells were harvested and lysed with a microfluidizer, the supernatants were concentrated with tangential flow filtration, and treated with benzonase (EMD Chemicals, Gibbstown, N.J.). The vector was purified by a three-step chromatography method involving group separation, anion exchange, and gel filtration before concentration by tangential flow filtration. Purified particles were formulated in phosphate-buffered saline containing 0.25% human serum albumin, vialed, and stored at −80° C. at a concentration of ~5×10$^{11}$ per-vg/ml. The stocks were characterized as described before. Vector titers were determined by a qPCR assay using primers spanning the HLP promoter. DNA standards for QPCR were prepared by linearizing the vector plasmid pssAAV-HLP-Atp7b with HincII.

Figure 3:
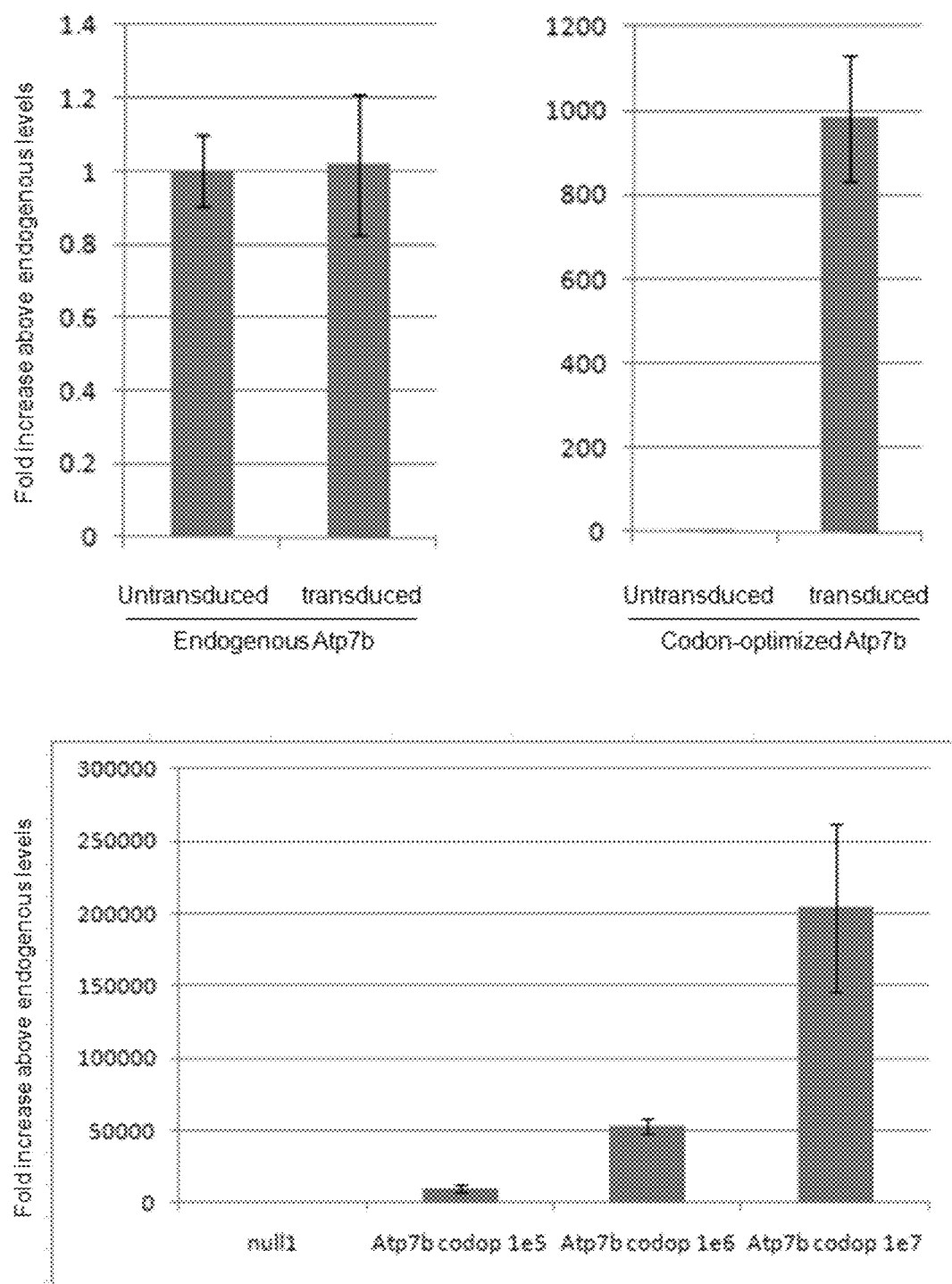

Assessment of vector activity in vitro: Huh7 liver cells were transduced in vitro with ssAAV-HLP-Atp7b vector at a dose of 5×10$^4$ vector genomes/cell (or untransduced as a control), or doses as shown in FIG. 3, and 72 hours later RNA was harvested using Trizol (Life technologies) as per the manufacturer's instructions. Superscript III (Life technologies) was then used to derive cDNA from this RNA, and used in quantitative polymerase chain reaction (QPCR) using SYBR green (Qiagen). The primers used to detect endogenous Atp7b were: 5' CACATGGCTCTGTGCT-CATT 3' (SEQ ID NO: 2) and 5' TCTGAGCCTCTTC-CACCAGT 3' (SEQ ID NO: 3). The primers used to detect codon optimized Atp7b were: 5' ACCG-GAAAACAGCTAGAGCA 3' (SEQ ID NO: 4) and 5' GTGGCTAGGCAGGACTTCAG 3' (SEQ ID NO: 5).

Animal studies: Long Evans Cinnamon rats (an established model for Wilson's disease) were maintained and bred by Dr. Sanjeev Gupta (Albert Einstein Institute, New York, USA). 7-9 week old animals were administered ssAAV-HLP-Atp7b vector by tail vein injection in a single dose. 7-28 days later (as mentioned) the animals were culled. Livers were assessed by western blotting and immunofluoresence for expression of Atp7b. Bile was collected by cannulation of the bile duct and copper levels were determined by flame absorption spectroscopy.

Alkaline gel electrophoresis: 800 mg of agarose is added to 98 ml deionized water and heated to dissolve. 2 ml of 50× alkaline electrophoresis buffer (2.5M NaOH, 50 mM EDTA in 500 ml deionized water) is added, the solution is mixed thoroughly and allowed to cool and set into a gel. The gel is placed in 1× alkaline electrophoresis buffer. 25 µl of various dilutions of the vector samples are mixed with 8.5 µl of 4× alkaline sample loading buffer (20% glycerol, 4× alkaline running buffer, 1.2% SDS, and xylene cyanol) and loaded onto the gel, which is run at 20V at 4° C. overnight. The next day, the gel is washed for 1 hour in 3× volumes of 0.1M Tris pH 8.0, and for 2 hours in 1× volumes of 0.1M NaCl with 4× GelRed in deionized water. The gel is rinsed quickly in tap water and visualized using a standard transilluminator. The "GeneSnap" and "GeneTools" programs from Syngene are used to quantitate the intensity of the bands of the vector genome, as well as DNA standards, from which the vector titre (genome copies/ml) can be estimated.

The invention claimed is:

1. A nucleic acid molecule comprising a nucleotide sequence encoding for a functional ATP7B protein wherein the nucleotide sequence has the sequence of SEQ ID NO.1.

2. A vector for expressing ATP7B protein, the vector comprising the nucleic acid molecule of claim 1.

3. The vector of claim 2, further comprising a liver specific promoter.

4. The vector of claim 2, wherein the vector is an AAV vector.

5. The vector of claim 2, wherein the vector is a single stranded vector.

6. A host cell comprising the nucleic acid molecule of claim 1.

7. A pharmaceutical composition comprising the nucleic acid molecule of claim 1, and one or more pharmaceutically acceptable excipients.

8. A pharmaceutical composition comprising the vector of claim 2, and one or more pharmaceutically acceptable excipients.

9. A method of treating Wilson's disease comprising administering a therapeutically effective amount of the vector of claim 2 to a patient suffering from Wilson's disease.

10. A method for delivery of a nucleotide sequence encoding ATP7B protein to a subject, which method comprises administering to the said subject the vector of claim 2.

* * * * *